United States Patent [19]

Alam et al.

[11] Patent Number: 4,879,308

[45] Date of Patent: Nov. 7, 1989

[54] AQUEOUS NITROGLYCERIN INJECTION AND MANUFACTURING PROCESS

[75] Inventors: Abu S. Alam, Libertyville; Utpal G. Joshi, Hanover Park; Jairaj U. Mehta, Forest Park; Fakrul A. A. Sayeed, Mundelein; John N. Kapoor, Lake Forest, all of Ill.

[73] Assignee: LyphoMed, Inc.

[21] Appl. No.: 84,631

[22] Filed: Aug. 11, 1987

[51] Int. Cl.$^4$ .............................................. A61K 31/21
[52] U.S. Cl. ..................................... 514/509; 514/970
[58] Field of Search ................................ 514/509, 970

[56] References Cited

U.S. PATENT DOCUMENTS

| | | | |
|---|---|---|---|
| 4,322,433 | 3/1982 | Leslie et al. | 424/298 |
| 4,323,577 | 4/1982 | Ohkuma et al. | 424/298 |
| 4,481,220 | 11/1984 | Giesselmann et al. | 424/349 |
| 4,746,506 | 5/1988 | Lynch | 424/2 |

FOREIGN PATENT DOCUMENTS 116944 8/1984 European Pat. Off. ............ 514/509

OTHER PUBLICATIONS

D. M. Baaske, A. H. Amann, D. M. Wagenknecht, M. Mooers, J. E. Carter, H. J. Hoyt and R. G. Stoll, "*Nitroglycerin Compatibility with Intravenous Fluid Filters, Containers and Admininstration Sets*", American Journal of Hospital Pharmacy, vol. 37, Feb. 1980, pp. 201–205.
A. J. Clarke and R. E. Watkins, "*Nitroglycerin Injection Manufactured by a Hospital Pharmacy*", American Journal of Hospital Pharmacy, vol. 42, Jul. 1985.
B. L. McNiff, E. F. McNiff and Ho-Leung Fung, "*Potency and Stability of Extemporaneous Nitroglycerin Infusions*", American Journal of Hospital Pharmacy, vol. 36, Feb. 1979, pp. 173–177.
D. M. Wagenknecht, D. M. Baaske, A. S. Alam, J. E. Carter and J. Shah, "*Stability of Nitroglycerin Solutions in Polyolefin and Glass Containers*", American Journal of Hospital Pharmacy, vol. 41, Sep. 1984, pp. 1807–1811.
A. Yacobi, A. H. Amann and D. M. Baaske, "*Pharmaceutical Considerations of Nitroglycerin*", Drug Intelligence and Clinical Pharmacy, vol. 17, Apr. 83, pp. 255–263.

Primary Examiner—Jacqueline V. Howard
Attorney, Agent, or Firm—Leydig, Voit & Mayer

[57] ABSTRACT

Nitroglycerin injection that is free of the customary organic solvents and has an extended shelf life of at least 1 year, consisting essentially of water, lactose, and nitroglycerin. Sodium chloride or dextrose may be added during manufacture or upon diluting with an infusion. Commerically safe manufacture and stable dispersion are assured by mixing lactose adsorbate, containing nitroglycerin, with water at high shear so that no nitroglycerin droplets coalesce. Stability is maintained by filtering and filling operations using nonreactive, nonleaching, nonadsorptive materials.

20 Claims, No Drawings

AQUEOUS NITROGLYCERIN INJECTION AND MANUFACTURING PROCESS

BACKGROUND OF THE INVENTION

1. Field of the Invention

The field of this invention comprises aqueous solutions of nitroglycerin that are intended for intravenous injection, processes for making such solutions, and the use of such solutions in the treatment of humans and other mammals, especially for treating cardiovascular disease.

2. Description of the Related Art Including Information Disclosed Under 37 C.F.R. §§ 1.97-1.99 (1987).

Aqueous nitroglycerin injection is a comparatively recent development. Although nitroglycerin has been used medically for over 100 years, and is administered today in a wide variety of forms, including sublingual tablets, cutaneous ointments and creams, transdermal pads, and intravenous injection solutions, injectable solutions have been in use for less than about 20 years. The comparatively recent development of nitroglycerin for injection may be explained in part by the sensitivity of nitroglycerin to percussive shock and its violent explosive properties upon detonation. A brief history of nitroglycerin's discovery will aide an understanding of the constraints imposed on the manufacture of aqueous nitroglycerin injection.

The name "nitroglycerin" can be used to refer to any nitrate of glycerol, but especially the trinitrate, the heavy, oily, explosive liquid invented in 1846 by Ascanio Sobrero. Nitroglycerin, or glycerol trinitrate, is also known chemically as 1,2,3-propanetriol; glyceryl trinitrate; glycerol nitric acid triester; nitroglycerol; trinitroglycerol; trinitrin; and glonoin; but is more descriptively called "blasting oil."

Nitroglycerin has the structure:

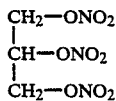

The stable form of nitroglycerin crystals melts in the temperate region of 55.4° F. (13° C.) and is extremely unstable as it thaws; liquid nitroglycerin will detonate if subjected to intense heat or percussion. Nitroglycerin is therefore most useful when its explosive properties are controlled, often by dispersing the compound in an inert substance. In 1867, Alfred Nobel mixed nitroglycerin with a nonexplosive, nonreactive, porous, siliceous earth, kieselguhr, and patented dynamite. While today's dynamite contains no pure nitroglycerin because it is too sensitive, pure nitroglycerin is readily available today for medical uses as an adsorbate in lactose powder.

The subsequent discovery of nitroglycerin's medical uses did not lessen its sensitivity to detonation by intense heat or shock. Although nitroglycerin is not used medically in explosive concentrations, it was the primary explosive ingredient of dynamite, and nitroglycerin's explosive properties control the commercial manufacture of drugs in which "blasting oil" is the active ingredient.

Nitroglycerin is an organic nitrate and, although poisonous if taken in large doses, in medical applications has the action of nitrites and is a vasodilator, widening the lumen, or cavity, of blood vessels. Nitroglycerin relaxes vascular smooth muscle tissue. Veins are dilated more than arteries, but both can be dilated depending on the dose. Dilation of the veins causes peripheral pooling of blood and decreases its return to the heart, reducing diastolic blood pressure. Relaxation of the arteries reduces resistance to blood flow from the heart, decreasing systolic blood pressure. Nitroglycerin is therefore excellent for opening temporarily clogged arteries during a heart attack, especially congestive heart failure associated with acute myocardial infarction. The arterial and venous effects of nitroglycerin reduce myocardial oxygen consumption, increasing oxygenation of the middle muscular layer of the heart, and nitroglycerin is therefore also useful for treating angina pectoris. Nitroglycerin finds additional utility in (1) controlling blood pressure in perioperative hypertension, or hypertension resulting from intratracheal intubation, anesthesia, skin incision, sternotomy, cardiac bypass, and postsurgical recovery, and (2) in producing controlled hypotension (induced low blood pressure) during surgery.

Just as Nobel made nitroglycerin more tractable in 1867 by dispersing the oil in kieselguhr, to make it less sensitive to shock, so mixing nitroglycerin in a lactose powder renders nitroglycerin safe to use: dynamite can be cut safely with a knife; nitroglycerin powders are easily transported. The danger lies in processing: If pure nitroglycerin separates out of the mixture then an explosion can occur. Accordingly, aqueous nitroglycerin injection has not been easily developed because of the attendant phase separation problems that can result in a pure nitroglycerin coming out of solution.

Nitroglycerin is only slightly soluble in water. Nitroglycerin, an oil, dissolves slowly in water, having a saturation concentration of only 1.25 milligrams of nitroglycerin per milliliter of water. The diffusivity of nitroglycerin in dilute solution in the solvent water at 20° C., a measure of the rate at which nitroglycerin molecules will intermingle with water molecules as a result of their spontaneous movement caused by thermal agitation, is only about $0.6 \times 10^{-5}$ square centimeters per second, as given by the empirical correlation of Wilke and Chang. Wilke, C.R.: *Chem. Eng. Progr.*, 45, 218 (1949) and Wilke, C.R., and P. Chang: *AIChEJ.* 1, 264 (1955). Not surprisingly then, the first commercial nitroglycerin solution for injection came on the market a scant 6 years ago, in 1981.

Several formulations of nitroglycerin injection are known in the art. The 1987 PHYSICIANS DESK REFERENCE ®, available from Medical Economics Co, Inc., at Oradell, N.J., 07649, discloses at least 4 companies that make or distribute nitroglycerin solutions for intravenous use. These products are sold under the tradenames TRIDIL ®, NITRO-BID IV ®, NITROSTAT IV ®, and NITROL IV ®. These are all concentrated drugs, not intended for direct intravenous injection, and each contains undesirable organic solvents. Each milliliter of TRIDIL ® contains either alcohol or alcohol and propylene glycol; each milliliter of NITRO-BID IV ® contains 45 milligrams propylene glycol dissolved in 70% ethanol; each milliliter of NITROSTAT IV ® contains 5% alcohol; each milliliter of NITROL IV ® contains dehydrated alcohol. These are all concentrated drugs that, when diluted, are chemically stable for only about 1 week, if refrigerated. The PDR ® discloses no commercially available aqueous nitroglycerin solution for injection that is stable for commercial purposes and contains no organic solvent such as alcohol or propylene glycol, which is undesirable for the patient. Stability for commercial purposes is at least 12 months, and, preferably, 24 months.

The patents that claim solutions of nitroglycerin teach that organic solubilizing agents are necessary in the processing of nitroglycerin to produce injection solutions. U.S. Pat. No. 4,323,577, issued Apr. 6, 1982, to Ohkuma et al., discloses a solution of nitroglycerin in the range of 0.1 to 1 milligrams of nitroglycerin per milliliter of solution, having at least one substance selected from among the sugars sorbitol, mannitol, and xylitol in the range of from 25 to 150 milligrams per milliliter of solution. Ohkuma et al. prepare the solution by first dissolving nitroglycerin in a volatile organic solvent such as ethanol, and then mixing the solution with a powder of sorbitol, mannitol, or xylitol, or a mixture of these. The ethanol is driven off, and the powder obtained thereby, containing 0.06 to 4% by weight of nitroglycerin, can be dissolved in water with stirring at high speed to develop the aqueous solution of nitroglycerin. Ohkuma et al. cite no danger of explosion and a high degree of stability for up to eight and one-half months. The solution becomes injectable if either filtered and sterilized by heat or filtered through a GS millipore filter. The solution can be used directly or can be mixed with an infusion solution.

Ohkuma et al. specifically teach away from the use of lactose powder containing nitroglycerin. Ohkuma teaches that intravenous nitroglycerin solutions prepared from a lactose powder have a low degree of stability for storage due to the presence of lactose. Furthermore, they relate that it is difficult to obtain any lactose warranted for the absence of pyrogen, or fever inducing substances, and the presence of antigenicity since lactose available in Japan is not intended for injection.

U.S. Pat. No. 4,481,220, issued Nov. 6, 1984, to Giesselmann et al., discloses a preparation of nitroglycerin that can be dissolved in water to form an isotonic nitroglycerin solution that is free of ethanol. Giesselmann made a "nitroglycerin solution having a concentration of approximately 1 mg of nitroglycerin/ml of solution without the separation of nitroglycerin droplets, by providing a small amount of an organic solubilizer customarily used for parenteral administration in conjunction with a solid nitroglycerin carrier," such as lactose. Col. 5, ll. 13-18. Giesselmann et al. disclose a list of organic solvents including alcohols, ethers, and acids.

Giesselmann et al. teach that it is impossible to manufacture aqueous injection on an industrial scale without resort to the use of organic solubilizers. See Col. 4, l. 65 through Col. 5, l. 6. Giesselmann et al. teach that where nitroglycerin is introduced into water on a water-soluble carrier the carrier dissolves and leaves a high local concentration of nitroglycerin above its saturation point. The droplets of oil coalesce and the danger of explosion that results makes the use of this process impossible for the manufacture of nitroglycerin solutions on an industrial scale. Giesselmann et al. of course solve this problem by the addition of organic solubilizing agents.

Hospital pharmacies can make extemporaneous nitroglycerin solutions by one of three methods: (1) dissolving nitroglycerin-containing sublingual tablets in water for injection, (2) dissolving commercially supplied lactose powder containing ten percent nitroglycerin in water for injection, or (3) diluting a commercially available nitroglycerin solution for intravenous injection.

Sublingual tablets contain nonvolatile organic solvents and excipients that affect dissolution and stability. For example, U.S. Pat. No. 3,873,727 issued Mar. 25, 1975, to Fusari et al. claims a process for making molded sublingual tablets where the stability of the tablets is improved by using an organic solvent such as polyethylene glycol in combination with a water soluble pharmaceutical carrier. Dissolution of such a tablet to form an injectable solution incorporates the organic solvent in the intravenous formulation. Furthermore, the USP specification for the content of sublingual nitroglycerin tablets is 80 to 120% of the labeled strength. Preparations of nitroglycerin injection made from sublingual tablets therefore vary substantially in potency.

Commercially available nitroglycerin solutions, such as those described in the PDR ®, contain alcohol, organic solvents, or both, as discussed above. These solvents are present in any of the extemporaneously produced hospital formulations made by diluting commercial injection.

One solvent-free aqueous nitroglycerin injection is known that can be produced in a hospital pharmacy. In July of 1985 the American Journal of Hospital Pharmacy reported that a hospital pharmacy can create an injectable nitroglycerin solution that is stable for up to 70 days and is free of organic solvents such as ethanol or propylene glycol by dissolving a powder that contains one part nitroglycerin and nine parts lactose in normal saline (0.9% sodium chloride) or 5% dextrose for injection. Clark, Allan J. and Raymond E. Watkins. Nitroglycerin Injection Manufactured By a Hospital Pharmacy. *Am J. Hosp. Pharm.* 1985; 42: 1542-6. The authors used a commercial powder adsorbate of nitroglycerin, 10% nitroglycerin and lactose, hydrous, USP, manufactured by ICI Americas, Inc., Wilmington, Del. 19897. After weighing the powder, it was placed in a 12 liter glass mixing flask, half filled with either 0.9% sodium chloride injection, USP, or 5% dextrose injection, USP. The lactose was dissolved by swirling the solution to create a pearl of nitroglycerin on the bottom of the flask. After adding a quantity of the base solution sufficient to bring the mixture to final volume, the mixture was stirred with a Lightnin' Stirrer, Series 20, which is a high speed mixer manufactured by VWR Scientific, Inc., for no less than 90 minutes.

Despite the development of a solvent-free aqueous nitroglycerin injection on a laboratory scale in a hospital pharmacy, no disclosure is made of such an injection that is producible on a commercial scale with a commercially useful shelf-life. Nitroglycerin saturates water at a concentration of only 1.25 milligrams per milliliter. Even when dispersed in lactose at a concentration of 10% nitroglycerin, the nitroglycerin is difficult to dissolve in water. The lactose dissolves immediately, leaving nitroglycerin oil droplets which quickly coalesce and result in a high local concentration of nitroglycerin above its saturation point. On a laboratory scale, such as a hospital pharmacy, where small batches of injection are prepared, the low solubility of nitroglycerin in water presents little difficulty. The lab technician simply dissolves the nitroglycerin pearl in the water/lactose solvent using a high speed mixer. It is not, however, possible to manufacture nitroglycerin solutions on an industrial scale using this process.

Until now, no method existed for making an aqueous solution of nitroglycerin, which is sterile, of adjustable tonicity, nonpyrogenic, directly injectable (ready-to-use) and dilutable, free of undesirable organic solvents, stable for at least 1 year and preferably for 2 years, and producible in a manner that is commercially useful. Salt or sugar may be added according to the needs of the patient at the time of the infusion. Dilution is a function of the fluid requirements of the patient, the expected duration of the infusion, and the responsiveness to the drug of the individual patient. There is no fixed optimum dose of nitroglycerin. Each patient must be titrated to the desired level of hemodynamic function, taking into account electrolyte requirements as well as the ability to metabolize sugars.

This invention provides a nitroglycerin solution that can be adapted to the individual patient's needs, that can be prepared on an industrial scale, that has a commercially useful shelf-life, and that contains no harmful organic solvents. Nitroglycerin is a highly explosive substance; the most advanced methods of hospital pharmacies are not safe enough to use on an industrial scale because they allow nitroglycerin to reach local concentrations above saturation.

Accordingly, it is an object of this invention to provide an aqueous solution of nitroglycerin that is suitable for intravenous injection and is stable for at least 1 year and preferably for 2 years. It is a further object of this invention to provide a nitroglycerin solution that is suitable for injection and can be adjusted for tonicity depending on the hemodynamic and fluid requirements of the individual. It is still another object of this invention to provide a ready-to-use and solvent-free aqueous solution of nitroglycerin that is adjusted for tonicity in that the base solution contains either saline or dextrose for injection.

Yet another object of the invention is to develop a process that is safe enough to be used commercially to manufacture aqueous solutions of nitroglycerin that contain no organic solvents and are stable for at least 1 year and preferably for 2 years.

SUMMARY OF THE INVENTION

The invention comprises an aqueous solution of nitroglycerin suitable for intravenous injection and stable for at least 1 year, preferably 2 years, that contains no organic solubilizing agent other than innocuous lactose. The stable, sterile, and nonpyrogenic aqueous nitroglycerin injection consists essentially of sterile water for injection, lactose, and nitroglycerin in an amount of from about 0.01 to about 1.0 milligrams of nitroglycerin per milliliter of solution. This aqueous formulation has no tonicity adjustment and may be further diluted with ¼, ½, or normal saline, or 2.5% or 5% dextrose for injection as necessary for electrolyte or sugar requirements or restrictions. Salt or sugar may be added to the formulation during manufacture or at the hospital where an extemporaneous infusion is made from the aqueous solution.

The invention includes a process for making the aqueous solution of nitroglycerin. The process comprises dissolving a mixture of nitroglycerin and lactose in sterile water for injection using high shear agitation sufficient to completely dissolve the nitroglycerin without allowing the nitroglycerin droplets to coalesce or to reach local concentrations above saturation. Sterile water for injection may be added with continuous agitation, as necessary to adjust the nitroglycerin concentration.

The solution is sterilized by filtering it through a 0.2 micron filter using a nonadsorptive tubing. In order to preserve the stability of the solution, sterile and depyrogenated glass vials or ampules are aseptically filled and then stoppered with nonreactive, nonleaching, elastomeric closures.

The nitroglycerin injection solution of the invention avoids cardiovascular side effects because it contains no organic solvent such as ethanol or propylene glycol. Furthermore the solution is commercially useful: as prepared, it is stable for at least 1 year and preferably for 2 years, and is a consistently sterile, pyrogen free, stable, quality controlled formulation of intravenous nitroglycerin. The process used to prepare the nitroglycerin formulation is safe enough to use commercially to produce nitroglycerin infusions on an industrial scale.

BEST MODE FOR CARRYING OUT THE INVENTION

The aqueous nitroglycerin injection of this invention is compounded from a commercial powder of 1 part nitroglycerin dispersed in 9 parts lactose. The 10% nitroglycerin in lactose, hydrous, USP, is available from ICI Americas, Inc., Wilmington, Del. 19897 and from Gyma Laboratories of America, Inc., 65 Commercial Avenue, Garden City, N.Y. 11530. The powder may lose potency over time and it is therefore advantageous to conduct an assay for potency to determine exactly the quantity required. An assay is recommended even when the powder is fresh since "ten percent" nitroglycerin is a nominal value and the assay will yield an exact figure.

In practicing the present invention, certain safety procedures should be followed. Protective apparel such as gowns, respirators, gloves, and goggles must be worn when working with nitroglycerin to avoid its toxic effects. The skin and mucus membranes readily absorb nitroglycerin and direct skin contact must therefore be avoided. Rapid adsorption through the skin makes nitroglycerin a useful drug for the treatment of angina pectoris in ointment form, but a hazardous poison for the healthy individual experiencing no oxygen deficiency in the myocardium. Symptoms of nitroglycerin poisoning are a pounding heart, flushed face, throbbing head, intense headache, nervousness, nausea, vomiting and fainting. The maximum allowable concentration in the work place is 0.5 parts per million of air.

According to a preferred process of this invention, about two-thirds or more of the water for injection, USP, required to form a solution of the desired volume, is placed into a mixing tank having a high speed stirrer. The tank is purged with nitrogen until the oxygen level in the tank falls below about 2 ppm. The nitrogen blanket should be maintained throughout the compounding process, and the mixture should be protected form light both before, during, and after the compounding. Then the 10% nitroglycerin/lactose powder is slowly added to the tank. The stirrer motor is started at a slow rate of speed at first, and then is increased gradually to the maximum so as not to create splashes. Areas where the product does not get mixed should be avoided. The product takes some time to dissolve, so mixing should continue until the nitroglycerin completely dissolves, typically about forty-five minutes. After the nitroglycerin completely dissolves, then the volume of the solution may be brought to the desired level by the addition of oxygen-free water for injection, USP. Sodium chloride or dextrose can be added to the mixing tank and mixed thoroughly with the solution either before or after the nitroglycerin in lactose is added to the tank. At this time it may be desirable to determine the physical properties of the solution.

The solution is preferably filtered through a sterile 0.22 micron filter into a clean sterile receiving jar. Filtration and filling should be carried out under aseptic conditions using strict aseptic technique. Preferred practice is to prefilter the solution with a nylon filter such as the Pall N66 0.45 micron filter, and then filter with another, smaller nylon filter, such as the Pall SLK 7002 NFP 0.2 micron filter. Such filters do not leach or shed any materials into the solution; they are completely nonreactive, and they do not adsorb nitroglycerin. The GS millipore filter, such as the millistat GS manufactured by Millipore Corp., Bedford, Mass. 10730, also is probably suitable, and has only 5% nitroglycerin adsorption. The filters should be tested for integrity at 15 psig before and after use.

The use of TYGON® tubing to transfer the nitroglycerin product should be avoided. TEFLON® and silicon medical grade tubing (SILASTIC® or similar tubing) may be used in practicing the present invention since they are nonshedding and nonleaching, are completely unreactive, and do not adsorb nitroglycerin. Polyethylene tubing having negligible adsorption of nitroglycerin is probably also suitable.

After filtering, the sterile solution is transferred through nonadsorptive tubing and aseptically filled into depyrogenated sterile glass vials or ampules. The glass vials are stoppered with a nonreactive, nonleaching, nonadsorptive elastomeric closure, such as a 28 mm IVPB stopper (Nos. 1711 and 1888 Gray) or a B0857F2-TST stopper. Glass vials or ampules are sterilized at 250° for 180 min.

For maximum stability, the product should be stored where it can be protected from light. It may be stored at room temperature, but it should not be stored at or below its freezing point. The product should be stored away from heat and any flammable material.

The mechanism by which the aqueous nitroglycerin injection of this invention has acquired a surprising and commercially useful stability, which is at least 1 and preferably 2 years, is not known at present. It is believed that the lactose acts as a dispersing agent at the moment the powder is introduced into the water. Before it dissolves, the lactose prevents coalescence of the very small droplets of absorbed nitroglycerin. In the practice of the present invention, no organic solubilizing agent other than innocuous lactose is used to increase the solubility of nitroglycerin in water. Instead, the nitroglycerin dispersion is stabilized through the use of mixing equipment capable of generating a fluid stream of high velocity with very great shear forces.

After dissolution is complete, saline or dextrose may be added if it is desired to adjust the tonicity of the solution to about 280 mOsm. The solution can be used as is, or may be adjusted subsequently, for example, during open heart surgery, when the fluid requirements and hemodynamic function of the individual are known. Optionally, one may dissolve the nitroglycerin lactose adsorbate in either 5% dextrose for injection or saline, using the same high-speed stirring equipment.

The following examples demonstrate the use of the process to produce aqueous nitroglycerin injection, free of harmful organic solvents that is stable for at least 1 year and preferably for 2 years. Of course, some of the steps may be varied without an appreciable effect on the formulation. Indeed, these examples are illustrative but not in limitation, of the invention.

EXAMPLE 1

Thirty liters of an aqueous nitroglycerin injection having a concentration of 0.5 mg/ml was prepared and filled into 100 ml flint molded sterile glass containers (CA-9262) with 28 mm IVPB stoppers (1711 Gray), in accordance with the following procedure. Nitroglycerin adsorbed onto lactose powder was obtained from Gyma Labs. Analysis of the powder showed that it contained 102.39% of its labelled nitroglycerin content of 10% nitroglycerin in lactose, so 147 grams of powder was weighed out.

About 22,000 ml of Water for Injection, USP, was placed into a mixing tank equipped with a stirrer. The solution was purged with nitrogen until the oxygen level reached 1.7 ppm. The powder (147 gms) was added slowly and the stirrer speed was gradually increased to maximum; stirring was maintained until complete dissolution occurred. Oxygen-free water for injection, USP was added in a quantity sufficient to yield final volume. The pH of the solution was determined to be 5.9. Then the solution was filtered through a 0.22 micron filter into clean and sterile vials, under aseptic conditions.

The vials, filled to 105.0 ml±1.0 ml, were stored away from heat and flammable materials in a cool, dry, and dark place. Stability data for storage at 4° C. over a 3 month period are as follows:

| month | 0 | 1 | 2 | 3 |
|---|---|---|---|---|
| pH | 6.2 | — | — | 5.9 |
| % assayed nitroglycerin | 102.1 | 102.1 | 101.4 | 103.6 |
| color | colorless | colorless | colorless | colorless |
| clarity | clear | clear | clear | clear |

Another set of vials were stored at a room temperature (15 to 30° C.), and were also found to be essentially stable over 3 months, as shown by the following data:

| month | 0 | 1 | 2 | 3 |
|---|---|---|---|---|
| pH | 6.2 | 5.7 | 5.8 | 6.3 |
| % assayed nitroglycerin | 102.1 | 100.4 | 99.3 | 106.3 |
| color | colorless | colorless | colorless | colorless |
| clarity | clear | clear | clear | clear |

Another set of vials were stored at an elevated temperature of 40° C., and were also found to be stable over 3 months, as shown by the following data:

| month | 0 | 1 | 2 | 3 |
|---|---|---|---|---|
| pH | 6.2 | 5.3 | 5.1 | 5.3 |
| % assayed nitroglycerin | 102.1 | 99.6 | 96.7 | 93.4 |
| color | colorless | colorless | colorless | colorless |
| clarity | clear | clear | clear | clear |

EXAMPLE 2

The same procedure as used in Example 1 was followed except for the use of a B0857F2-TST stopper in the same glass vial as used in example 1, and similar results were obtained after storage of the solution. The stability results for the samples stored at 4° C. are as follows:

| month | 0 | 1 | 2 | 3 |
|---|---|---|---|---|
| pH | 6.2 | — | — | 6.0 |
| % assayed nitroglycerin | 102.1 | — | — | 103.7 |
| color | colorless | colorless | colorless | colorless |
| clarity | clear | clear | clear | clear |

The samples, stored at a room temperature (15 to 30° C.), also remained essentially stable over 3 months, as shown by the following results:

| month | 0 | 1 | 2 | 3 |
|---|---|---|---|---|
| pH | 6.2 | — | 6.0 | 6.0 |
| % assayed nitroglycerin | 102.1 | — | — | 102.9 |
| color | colorless | colorless | colorless | colorless |
| clarity | clear | clear | clear | clear |

The samples, stored at an elevated temperature of 40° C., also remained stable over 3 months, as shown by the following results:

| month | 0 | 1 | 2 | 3 |
|---|---|---|---|---|
| pH | 6.2 | — | 5.1 | 5.2 |
| % assayed nitroglycerin | 102.1 | — | — | 100.1 |
| color | colorless | colorless | colorless | colorless |
| clarity | clear | clear | clear | clear |

EXAMPLE 3

The same procedure as in Example 1 was followed, except for the use of a 28 mm IVPB stopper (1888 Gray) in the same glass vial used in Example 1, and produced similar results upon storage of the solution at 4° C.

| month | 0 | 1 | 2 | 2 |
|---|---|---|---|---|
| pH | 6.3 | 6.4 | — | 5.5 |
| % assayed nitroglycerin | 108.4 | 107.1 | 108.4 | 109.0 |
| color | colorless | colorless | colorless | colorless |
| clarity | clear | clear | clear | clear |

The solutions, which were stored at a room temperature (15 of 30° C.), also remained essentially stable over 3 months, as shown by the following data:

| month | 0 | 1 | 2 | 3 |
|---|---|---|---|---|
| pH | 6.3 | 6.1 | 6.0 | 5.5 |
| % assayed nitroglycerin | 108.4 | 106.9 | 108.3 | 108.7 |
| color | colorless | colorless | colorless | colorless |
| clarity | clear | clear | clear | clear |

The solutions, which were stored at an elevated temperature of 40° C., also remained stable over 3 months, as shown by the following data:

| month | 0 | 1 | 2 | 3 |
|---|---|---|---|---|
| pH | 6.3 | 5.6 | 5.2 | 4.8 |
| % assayed nitroglycerin | 108.4 | 105.7 | 107.9 | 106.0 |
| color | colorless | colorless | colorless | colorless |
| clarity | clear | clear | clear | clear |

The solutions, which were stored at an elevated temperature of 55° C., also remained stable over 1 month (longer times not being investigated), as shown by the following data:

| month | 0 | 1 |
|---|---|---|
| pH | 6.3 | 4.6 |
| % assayed nitroglycerin | 108.4 | 101.7 |
| color | colorless | colorless |
| clarity | clear | clear |

EXAMPLE 4

Ten liters of an aqueous nitroglycerin injection comprising 0.9% sodium chloride and having a concentration of 0.5 mg nitroglycerin per ml of injection was prepared using the procedure discussed below, and filled into 100 ml flint molded sterile glass containers (CA-9262) with 28 mm IVPB stoppers (1711 Gray). An assay of nitroglycerin/lactose powder obtained from Gyma Labs showed that it contained 102.39% of its labelled nitroglycerin content of 10% nitroglycerin in lactose. Therefore the amount of powder employed was 48.8 grams.

A mixing tank equipped with a Lightnin' stirrer manufactured by VWR Scientific, Inc., Model No. V-7, Ser. No. 86/8090421 containing sterile water for injection, was purged with nitrogen until the oxygen level dropped to 1.9 ppm. Exactly 90.0 grams of NaCl was then added to produce a concentration of 9.0 mg/ml of solution. The NaCl took 18 minutes to dissolve, and then the nitroglycerin powder (48.8 gms) was added slowly. The stirrer motor was started slowly and gradually increased to the maximum to avoid splashes. It took 38 minutes to completely dissolve the nitroglycerin, and then oxygen-free water was added to bring the solution up to 10 liters. After the pH was checked at 5.9, the solution was filtered through a 0.22 micron filter into clean and sterile vials under aseptic conditions.

The vials, filled to 105 ml ± 1.0 ml, were stored away from heat and flammable materials in a cool, dry, and dark place. Stability data for the vials stored at 4° C. over a 3 month period are as follows:

| month | 0 | 1 | 2 | 3 |
|---|---|---|---|---|
| pH | 6.0 | — | — | 5.6 |
| % assayed nitroglycerin | 101.5 | 101.5 | 99.4 | 102.5 |
| color | colorless | colorless | colorless | colorless |
| clarity | clear | clear | clear | clear |

A portion of the vials was stored at a room temperature (15 to 30° C.), and the solution remained essentially stable over 3 months as shown by the following data:

| month | 0 | 1 | 2 | 3 |
|---|---|---|---|---|
| pH | 6.0 | 5.9 | 5.7 | 5.5 |
| % assayed nitroglycerin | 101.5 | 100.1 | 96.5 | 100.7 |

| month | 0 | 1 | 2 | 3 |
|---|---|---|---|---|
| color | colorless | colorless | colorless | colorless |
| clarity | clear | clear | clear | clear |

Another portion of the vials was stored at an elevated temperature of 40° C., and the solution remained stable over 3 months as shown by the following data:

| month | 0 | 1 | 2 | 3 |
|---|---|---|---|---|
| pH | 6.0 | 5.3 | 5.3 | 5.0 |
| % assayed nitroglycerin | 101.5 | 97.9 | 96.5 | 97.5 |
| color | colorless | colorless | colorless | colorless |
| clarity | clear | clear | clear | clear |

EXAMPLE 5

Ten liters of an aqueous nitroglycerin injection comprising 5% dextrose and having a concentration of 0.5 mg nitroglycerin per ml of injection was prepared in accordance with the following procedure and filled into 100 ml flint molded sterile glass containers (CA-9262) with 28 mm IVPB stoppers (1711 Gray). Nitroglycerin/lactose powder was obtained from Gyma Labs and analysis of the powder showed that it contained 102.39% of its labeled nitroglycerin content of 10% nitroglycerin in lactose. Therefore, 48.8 grams of the powder was required.

The same procedure was followed as that in Example 4, except that dextrose, in place of sodium chloride, was added after the mixing tank was purged of oxygen to a level of 1.8 ppm. The dextrose took 20 min to dissolve, and then the nitroglycerin was dissolved over about 32 minutes. After complete mixing, oxygen-free water was added to bring the solution up to volume and the pH was checked at 5.8. Filtering and filling were carried out as in Example 4.

The vials, filled to 105 ml±1.0 ml, were stored away from heat and flammable materials in a cool, dry, and dark place. Stability data for the vials stored at 4° C. over a 3 month period are as follows:

| month | 0 | 1 | 2 | 3 |
|---|---|---|---|---|
| pH | 5.9 | — | — | 5.4 |
| % assayed nitroglycerin | 107.7 | 106.7 | 104.3 | 108.8 |
| color | colorless | colorless | colorless | colorless |
| clarity | clear | clear | clear | clear |

A portion of the vials was stored at a room temperature (15 to 30° C.), and the solution remained essentially stable over 3 months as shown by the following data:

| month | 0 | 1 | 2 | 3 |
|---|---|---|---|---|
| pH | 5.9 | 5.7 | 5.6 | 5.4 |
| % assayed nitroglycerin | 107.7 | 105.9 | 103.7 | 106.3 |
| color | colorless | colorless | colorless | colorless |
| clarity | clear | clear | clear | clear |

Another portion of the vials was stored at an elevated temperature of 40° C., and the solution remained stable over 3 months as shown by the following data:

| month | 0 | 1 | 2 | 3 |
|---|---|---|---|---|
| pH | 5.9 | 5.1 | 4.9 | 4.7 |
| % assayed nitroglycerin | 107.7 | 104.2 | 102.2 | 101.0 |
| color | colorless | colorless | colorless | colorless |
| clarity | clear | clear | clear | clear |

We claim:

1. An aqueous solution of nitroglycerin that is sterile, nonpyrogenic, adjustable for tonicity, and suitable for intravenous injection in mammals requiring treatment with nitroglycerin consisting essentially of sterile water for injection, lactose, and nitroglycerin, said nitroglycerin being present at a concentration of at least about 0.5 mg/ml; the solution containing no organic solvents and being stable for at least 1 year.

2. The aqueous solution of nitroglycerin as claimed in claim 1 wherein the nitroglycerin is present in the solution in an amount of from about 0.5 to about 1.0 milligrams of nitroglycerin per milliliter of solution.

3. An aqueous solution of nitroglycerin that is sterile, nonpyrogenic, adjusted for tonicity, and suitable for intravenous injection in mammals requiring treatment with nitroglycerin consisting essentially of sterile water for injection, lactose, sodium chloride, and nitroglycerin, said nitroglycerin being present at a concentration of at least 0.5 mg/ml; the solution containing no organic solvents and being stable for at least 1 year.

4. The aqueous solution of nitroglycerin as claimed in claim 3 wherein the nitroglycerin is present in the solution in an amount of from about 0.5 to about 1.0 milligrams of nitroglycerin per milliliter of solution.

5. An aqueous solution of nitroglycerin that is sterile, nonpyrogenic, adjusted for tonicity, and suitable for intravenous injection in mammals requiring treatment with nitroglycerin consisting essentially of sterile water for injection, lactose, dextrose, and nitroglycerin, said nitroglycerin being present at a concentration of at least about 0.5 mg/ml; the solution containing no organic solvents and being stable for at least 1 year.

6. The aqueous solution of nitroglycerin as claimed in claim 5 wherein the nitroglycerin is present in the solution in an amount of from about 0.5 to about 1.0 milligrams of nitroglycerin per milliliter of solution.

7. An aqueous solution of nitroglycerin that is sterile, nonpyrogenic, and suitable for use in intravenous injection in mammals requiring treatment with nitroglycerin, consisting essentially of (1) a solvent selected from the group comprising sterile water for injection, saline solution and dextrose solution, (2) lactose, and (3) nitroglycerin, said nitroglycerin being present at a concentration of at least about 0.5 mg/ml; the solution containing no organic solvents other than lactose and being stable for at least 1 year.

8. The aqueous solution of nitroglycerin as claimed in claim 7 wherein the nitroglycerin is present in the solution in an amount of from about 0.5 to about 1.0 milligrams of nitroglycerin per milliliter of solution.

9. A sterile and nonpyrogenic aqueous solution of nitroglycerin that is stable for at least 1 year and consists essentially of nitroglycerin, said nitroglycerin being present at a concentration of at least about 0.5 mg/ml, water, and a component selected from the group consisting of lactose, lactose and sodium chloride, and lactose and dextrose.

10. The aqueous solution of nitroglycerin as claimed in claim 9 wherein the nitroglycerin is present in the solution in an amount of from about 0.5 to about 1.0 milligrams of nitroglycerin per milliliter of solution.

11. A process for making an aqueous solution of nitroglycerin that is sterile, nonpyrogenic, and therefore suitable for intravenous injection in mammals requiring treatment with nitroglycerin, comprising:
 a. dissolving a mixture of nitroglycerin and lactose in sterile water for injection using high shear agitation sufficient to completely dissolve the nitroglycerin without allowing nitroglycerin droplets to coalesce or to reach local concentrations above saturation,
 b. adding sterile water for injection as necessary to adjust the nitroglycerin concentration using continuous agitation,
 c. filtering the solution to sterilize it through a filter using nonadsorptive tubing,
 d. aseptically filling sterile, depyrogenated, glass ampules or glass vials, and
 e. stoppering the glass vials or ampules with nonreactive, nonleaching elastomeric closures.

12. The process of claim 11 wherein a nitrogen blanket over the mixture is maintained throughout the process.

13. The process of claim 11 wherein the mixture of nitroglycerin and lactose comprises 1 part nitroglycerin and 9 parts lactose.

14. The process of claim 11 wherein the mixture of nitroglycerin and lactose is a powder that comprises less than 1 part nitroglycerin in 9 parts lactose.

15. The process of claim 14 wherein a quantity of the nitroglycerin and lactose mixture is dissolved in water sufficient to form a solution having a concentration of nitroglycerin of from about 0.5 to about 1.0 milligram of nitroglycerin per milliliter of water.

16. The process of claim 11 wherein a component selected from the group consisting of sodium chloride and dextrose is added to the solution after step (a) and before step (b), using continuous agitation.

17. The process of claim 11 wherein the sterile water for injection of step 1 further comprises sodium chloride.

18. The process of claim 11 wherein the sterile water for injection of step 1 further comprises dextrose.

19. The process of claim 11 wherein the solution is filtered through a 0.2 micron filter.

20. The process of claim 19 wherein the solution is filtered through a 0.45 micron prefilter before being filtered through a 0.2 micron filter.

* * * * *